US009723971B2

(12) United States Patent
Itai (10) Patent No.: US 9,723,971 B2
(45) Date of Patent: Aug. 8, 2017

(54) IMAGE PROCESSING APPARATUS, METHOD, AND PROGRAM

(71) Applicant: FUJIFILM Corporation, Tokyo (JP)

(72) Inventor: Yoshinori Itai, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 64 days.

(21) Appl. No.: 13/751,759

(22) Filed: Jan. 28, 2013

(65) Prior Publication Data

US 2013/0137926 A1     May 30, 2013

Related U.S. Application Data

(63) Continuation of application No. PCT/JP2011/004183, filed on Jul. 25, 2011.

(30) Foreign Application Priority Data

Jul. 28, 2010   (JP) ................................ 2010-168872

(51) Int. Cl.
| | |
|---|---|
| *A61B 1/04* | (2006.01) |
| *A61B 1/00* | (2006.01) |
| *G06T 15/08* | (2011.01) |
| *G06T 19/00* | (2011.01) |
| *A61B 6/00* | (2006.01) |
| *A61B 1/31* | (2006.01) |
| *G06T 7/00* | (2017.01) |

(52) U.S. Cl.
CPC ........ *A61B 1/00009* (2013.01); *A61B 1/0005* (2013.01); *A61B 1/04* (2013.01);
(Continued)

(58) Field of Classification Search
CPC ..... A61B 5/0035; A61B 5/004; A61B 5/0073; A61B 1/31; G06T 2207/30028; G06T 2207/30092; G06T 2219/028

USPC .................................................. 600/111, 118
See application file for complete search history.

(56) References Cited

U.S. PATENT DOCUMENTS 5,274,551 A * 12/1993 Corby, Jr. ..................... 600/433
5,776,050 A * 7/1998 Chen et al. .................... 600/117
(Continued)

FOREIGN PATENT DOCUMENTS

| CN | 101404923 | 4/2009 |
| JP | 2001-076184 | 3/2001 |

(Continued)

OTHER PUBLICATIONS

JP Office Action dated Oct. 29, 2013, with partial English translation; Application No. 2010-168872.
(Continued)

*Primary Examiner* — Anhtuan T Nguyen
*Assistant Examiner* — Jae Woo
(74) *Attorney, Agent, or Firm* — Young & Thompson (57) ABSTRACT

Obtaining a surface image captured by an endoscope inserted in a tubular organ associated with a surrounding blood vessel and representing an inner surface of a wall of the organ, generating, from a three-dimensional image representing a three-dimensional area including the organ, an adjacent blood vessel image depicting a portion of the blood vessel adjacent to the wall from a viewpoint in the three-dimensional image corresponding the viewpoint of the surface image, generating, from a three-dimensional image representing a three-dimensional area including a surrounding area of the organ, a surrounding blood vessel image depicting the blood vessel from a viewpoint in the three-dimensional image corresponding the viewpoint of the surface image, and causing the surface image, adjacent blood vessel image, and surrounding blood vessel image to be displayed in this order on a display unit.

16 Claims, 5 Drawing Sheets

(52) U.S. Cl.
CPC ............... *A61B 1/31* (2013.01); *A61B 6/504* (2013.01); *A61B 6/5247* (2013.01); *G06T 7/0012* (2013.01); *G06T 15/08* (2013.01); *G06T 19/00* (2013.01); *G06T 2207/10068* (2013.01); *G06T 2207/30028* (2013.01); *G06T 2207/30092* (2013.01); *G06T 2207/30101* (2013.01); *G06T 2210/41* (2013.01); *G06T 2219/028* (2013.01)

(56) References Cited

U.S. PATENT DOCUMENTS

| | | | | |
|---|---|---|---|---|
| 5,782,762 | A | * | 7/1998 | Vining .......................... 600/407 |
| 6,293,911 | B1 | * | 9/2001 | Imaizumi et al. ............ 600/160 |
| 6,591,130 | B2 | * | 7/2003 | Shahidi ......................... 600/424 |
| 8,672,836 | B2 | * | 3/2014 | Higgins et al. ............... 600/117 |
| 2003/0071894 | A1 | * | 4/2003 | Higuchi et al. ................ 348/65 |
| 2003/0176768 | A1 | * | 9/2003 | Gono et al. ................... 600/109 |

FOREIGN PATENT DOCUMENTS

| | | |
|---|---|---|
| JP | 2006-061274 | 3/2006 |
| JP | 2009-022411 | 2/2009 |

OTHER PUBLICATIONS

Chinese Office Action, dated Aug. 5, 2014, in corresponding Chinese Patent Application No. 201180036593.1.
Chinese Official Action—201180036593.1—Apr. 3, 2015.

* cited by examiner

IMAGE PROCESSING APPARATUS, METHOD, AND PROGRAM

TECHNICAL FIELD

The present invention relates to an image processing apparatus, method, and program for displaying an image for observing an organ, such as a large intestine or a stomach.

BACKGROUND ART

Heretofore, a technology for diagnosing and treating an organ of a patient, such as a large intestine or a stomach, using a real endoscopic image captured by an endoscope inserted in the organ has been known. Further, a technology for generating a virtual endoscopic image from a three-dimensional volume image obtained by CT imaging or the like and displaying the generated image has also been known.

Japanese Unexamined Patent Publication No. 2006-061274 proposes a method in which the position and orientation of an endoscope inserted into an organ are detected, then a virtual endoscopic image having the same field of view as the real endoscopic image is generated based on the detected position and orientation, and the real endoscopic image obtained by the endoscope is texture mapped to the virtual endoscopic image, whereby an image for display is generated.

DISCLOSURE OF INVENTION

When diagnosing and treating an organ such as a large intestine or a stomach, it is sometimes necessary to examine a surrounding blood vessel associated with the organ, as well as a three-dimensional structure and texture on a mucosal surface.

In the case of a large intestine, for example, the appearance of a blood vessel supplying nourishment to a lesion, such as a polyp, detected on the surface of the large intestine is a key factor for distinguishing large intestine cancer, and the appearance of the middle colic artery and right colic artery influences surgical planning of the large intestine cancer. Thus, when diagnosing or treating a large intestine, it is required to observe the appearance of capillary blood vessels located in the submucosal layer and intrinsic muscle layer, as well as on the mucosal surface, and succeeding vessels of the middle colic artery, right colic artery, ileocolic artery and the like.

In contrast, in the image for display provided by the technique described in Japanese Unexamined Patent Publication No. 2006-061274, the state of the mucosal surface of an organ may be observed, but the appearance of surrounding blood vessels associated with the organ may not be observed, so that the image cannot be said to appropriately respond to the needs described above.

The present invention has been developed in view of the circumstances described above, and it is an object of the present invention to provide an image processing apparatus, method, and program capable of providing an image suitable for observing a tubular organ associated with a surrounding blood vessel.

An image processing apparatus of the present invention is an apparatus for displaying an image for observing a tubular organ associated with a surrounding blood vessel, the apparatus including:

a surface image obtaining means for obtaining a surface image representing an inner surface of a wall of the organ captured by an endoscope inserted in the organ;

an adjacent image generation means for generating an adjacent blood vessel image from a three-dimensional image representing a three-dimensional area including the organ, the adjacent blood vessel image being an image depicting a portion of the blood vessel adjacent to the wall from a viewpoint in the three-dimensional image corresponding the viewpoint of the surface image;

a surrounding image generation means for generating a surrounding blood vessel image from a three-dimensional image representing a three-dimensional area including a surrounding area of the organ, the surrounding blood vessel image being an image depicting the blood vessel from a viewpoint in the three-dimensional image corresponding the viewpoint of the surface image; and a display control means for causing the surface image, adjacent blood vessel image, and surrounding blood vessel image to be displayed in this order on a display means.

The apparatus described above may include a lesion detection means for detecting a lesion from the surface image, and the display control means may be a means that causes the image display to be performed when a lesion is detected by the lesion detection means.

Further, the apparatus described above may include an instruction detection means for detecting an input that instructs execution of the image display; and the display control means may be a means that causes the image display to be performed when the input is detected by the instruction detection means.

The display control means may be a means that causes the surface image, adjacent blood vessel image, and surrounding blood vessel image to be displayed in a switched manner or side by side.

The surface image may be either one or both of an image captured when white light is directed to the surface and an image captured when light in a specific wavelength range different from the white light is directed to the surface.

The adjacent blood vessel image may be an image representing the portion of the blood vessel projected onto a structure of the organ.

An image processing method of the present invention is a method for displaying an image for observing a tubular organ associated with a surrounding blood vessel, the method including:

a surface image obtaining process for obtaining a surface image representing an inner surface of a wall of the organ captured by an endoscope inserted in the organ;

an adjacent image generation process for generating an adjacent blood vessel image from a three-dimensional image representing a three-dimensional area including the organ, the adjacent blood vessel image being an image depicting a portion of the blood vessel adjacent to the wall from a viewpoint in the three-dimensional image corresponding the viewpoint of the surface image;

a surrounding image generation process for generating a surrounding blood vessel image from a three-dimensional image representing a three-dimensional area including a surrounding area of the organ, the surrounding blood vessel image being an image depicting the blood vessel from a viewpoint in the three-dimensional image corresponding the viewpoint of the surface image; and a display control process for causing the surface image, adjacent blood vessel image, and surrounding blood vessel image to be displayed in this order on a display means.

The method described above may include a lesion detection process for detecting a lesion from the surface image, and the display control process may be a process that causes the image display to be performed when a lesion is detected by the lesion detection process.

An image processing program of the present invention is a program for causing at least one computer to perform processing performed by each means of the image processing apparatus described above. The program is recorded on a recording medium, such as CD-ROM, DVD, or the like, or otherwise stored in an auxiliary storage of a server computer or network storage in a downloadable manner and supplied to the user.

The term "adjacent to the wall" as used herein refers to an area within a predetermined range from the inner surface of the wall to outside.

The term "causing the surface image, adjacent blood vessel image, and surrounding blood vessel image to be displayed in this order" as used herein has a broad meaning of display performed in a manner in which the user receiving the display may recognize these images in the order in which they are displayed. For example, a display mode in which the surface image, adjacent blood vessel image, and surrounding blood vessel image are displayed in a switched manner and a display mode in which the surface image, adjacent blood vessel image, and surrounding blood vessel image are displayed side by side so as to be recognized by the user in this order by moving the visual line of the user on the display screen are included.

The term "surrounding area of the organ" as used herein refers to an area having a sufficient size to include at least a major blood vessel associated with the organ.

According to the image processing apparatus, method, and program of the present invention, a surface image representing an inner surface of a wall of the organ captured by an endoscope inserted in the organ is obtained, an adjacent blood vessel image is generated from a three-dimensional image representing a three-dimensional area including the organ, the adjacent blood vessel image being an image depicting a portion of the blood vessel adjacent to the wall from a viewpoint in the three-dimensional image corresponding the viewpoint of the surface image, a surrounding blood vessel image is generated from a three-dimensional image representing a three-dimensional area including a surrounding area of the organ, the surrounding blood vessel image being an image depicting the blood vessel from a viewpoint in the three-dimensional image corresponding the viewpoint of the surface image, and the surface image, adjacent blood vessel image, and surrounding blood vessel image are caused to be displayed in this order on a display means. This allows the appearance of the inner surface of the organ and the appearance of a blood vessel running from the surface to an outer periphery to be observed continuously whereby the relationship between a tissue on the inner surface of the organ and a surrounding blood vessel associated with the organ may be understood easily.

In the case where a lesion, such as a polyp or the like, is observed, in particular, this allows the appearance of a blood vessel supplying nourishment to the lesion and the running of the succeeding major blood vessel, as well as the appearance of the lesion on the mucosal surface, to be observed easily, thereby facilitating a determination as to whether the lesion is benign or malignant and surgical planning.

BEST MODE FOR CARRYING OUT THE INVENTION

Hereinafter, embodiments of the image processing apparatus, method, and program of the present invention will be described with reference to the accompanying drawings.

Figure 1:
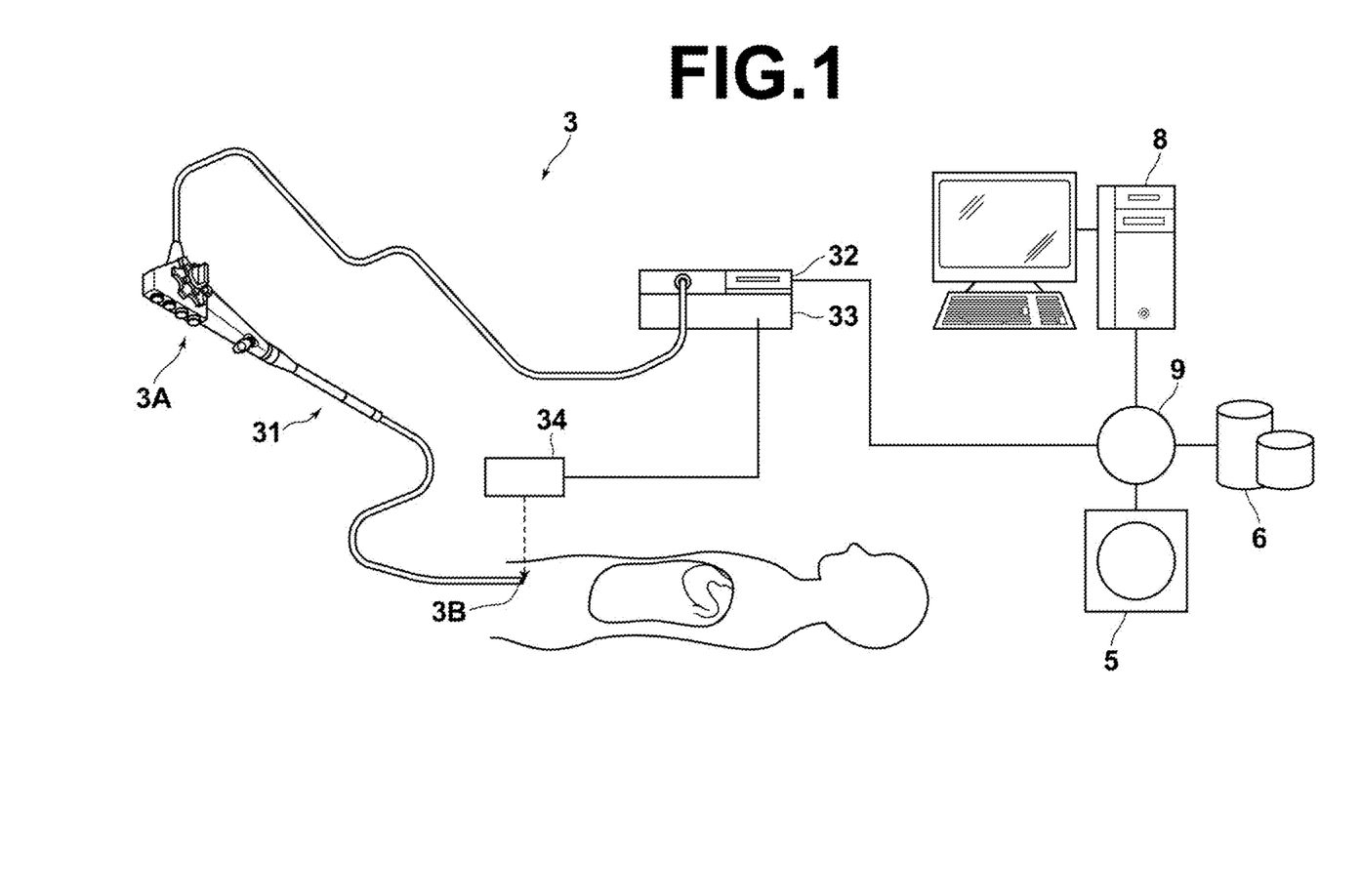
FIG. 1 is a hardware configuration diagram of a medical image processing system, illustrating an overview thereof.

FIG. 1 is a hardware configuration diagram of a medical image processing system, illustrating an overview thereof. As illustrated in FIG. 1, an endoscope apparatus 3, a three-dimensional image capturing apparatus 5, an image storage server 6, and an image processing apparatus 8 are communicatively linked to each other via network 9 in the system.

The endoscope apparatus 3 includes an endoscope 31 that captures an image of a body cavity of a subject, a processor unit 32 that generates an image of a subject tissue in the body cavity based on a signal obtained by image capturing, a light source unit 33 that supplies light for illuminating inside of the body cavity, a position detection unit 34 that detects the position and orientation of a tip portion of the endoscope 31.

The endoscope 31 includes an operation section 3A and an insertion section connected to each other, and has a universal cord extended and detachably attached to the processor unit 32 and light source unit 33. The operation section 3A has various types of buttons, such as a button for instructing a tip portion 3B of the insertion section to bend up-down and left-right directions within a predetermined angle range and the like. In the present embodiment, the endoscope 31 is a flexible scope for large intestines and is to be inserted into the large intestine of a subject. Light guided through an optical fiber from the light source unit 33 is projected from the tip portion 3B of the endoscope 31 and an image of the abdominal cavity of the subject is obtained by an image capturing optical system of the endoscope 31.

The light source unit 33 includes a white light source that emits white light with wavelengths in the range from red region to blue region and a narrow band light source that emits light with a specific wavelength different from the white light, such as light with a wavelength of 560±10 nm. The light source unit 33 is configured such that the light generated by the white light source is supplied if the image capturing mode of the endoscope apparatus 3 is ordinary image capturing mode while if the image capturing mode is spectral image capturing mode, the light generated by the narrow band light source is supplied to a light guide of the scope via an optical system.

The position detection unit 34 detects the position and orientation of the tip portion 3B of the endoscope 31. More specifically, the position detection unit 34 detects a relative position and orientation of the tip portion of the endoscope 31 inside of the subject by detecting the characteristic shape of the tip of the endoscope 31 with an echo unit having a detection area of three-dimensional coordinate system with the position of a specific region of a subject as the reference point, and supplies information of the obtained position and orientation of the tip portion 3B to the processor unit 32 as described, for example, in Japanese Unexamined Patent Publication No. 2006-061274. The position and orientation of the tip portion 3B correspond to the viewpoint and visual line direction.

The processor unit 32 generates an endoscopic image by converting an image signal captured by the endoscope 31 to a digital image signal and performing image quality correction through digital signal processing, such as white balance correction, shading correction, and the like. The processor unit 32 generates an ordinary endoscopic image E1 based on an image signal captured during the image capturing mode of the endoscope apparatus 3 is ordinary image capturing mode and a spectral endoscopic image E2 based on an image signal captured during the image capturing mode of the endoscope apparatus 3 is spectral image capturing mode. Each of the endoscopic images E1 and E2 is transmitted to the image storage server 6 and image processing apparatus 8 after information of the position and orientation of the tip portion 3B at the time of the image capturing is attached as auxiliary information.

The three-dimensional image capturing apparatus 5 is an apparatus that captures an image of an inspection target region of a subject and generates a three-dimensional image representing the region and, more specifically, the apparatus is a CT apparatus, MRI apparatus, PET, ultrasonograph, and the like. The three-dimensional image generated by the three-dimensional image capturing apparatus 5 is transmitted to the image storage server 6 and stored therein. In the present embodiment, a three-dimensional image V of an inspection target region, including at least the large intestine and a surrounding area thereof, is generated.

The image storage server 6 is a computer that stores and manages various types of data, and includes a large capacity external storage device and database management software. The image storage server 6 communicates with other apparatuses via the network 9 to send and receive image data and the like. More specifically, the image storage server 6 obtains an endoscopic image obtained by the endoscope apparatus 3 and a three-dimensional image obtained by the three-dimensional image capturing apparatus 5 via the network 9, and stores/manages them in a recording medium, such as the large capacity external storage device.

The storage format of image data and communication between each apparatus via the network 9 are based on a protocol, such as DICOM or the like.

Image processing apparatus 8 is a computer on which an image processing program of the present invention is installed. The computer may be a workstation or personal computer directly operated by a diagnostician, or a server computer linked thereto via the network. The image processing program is distributed stored in a recording medium, such as DVD, CD-ROM, or the like, and installed on the computer from the recording medium. Otherwise, the program is stored in a storage device of a server computer connected to the network or in a network storage in a manner accessible from outside and down-loaded/installed on a computer used by the doctor in response to a request.

Figure 2:
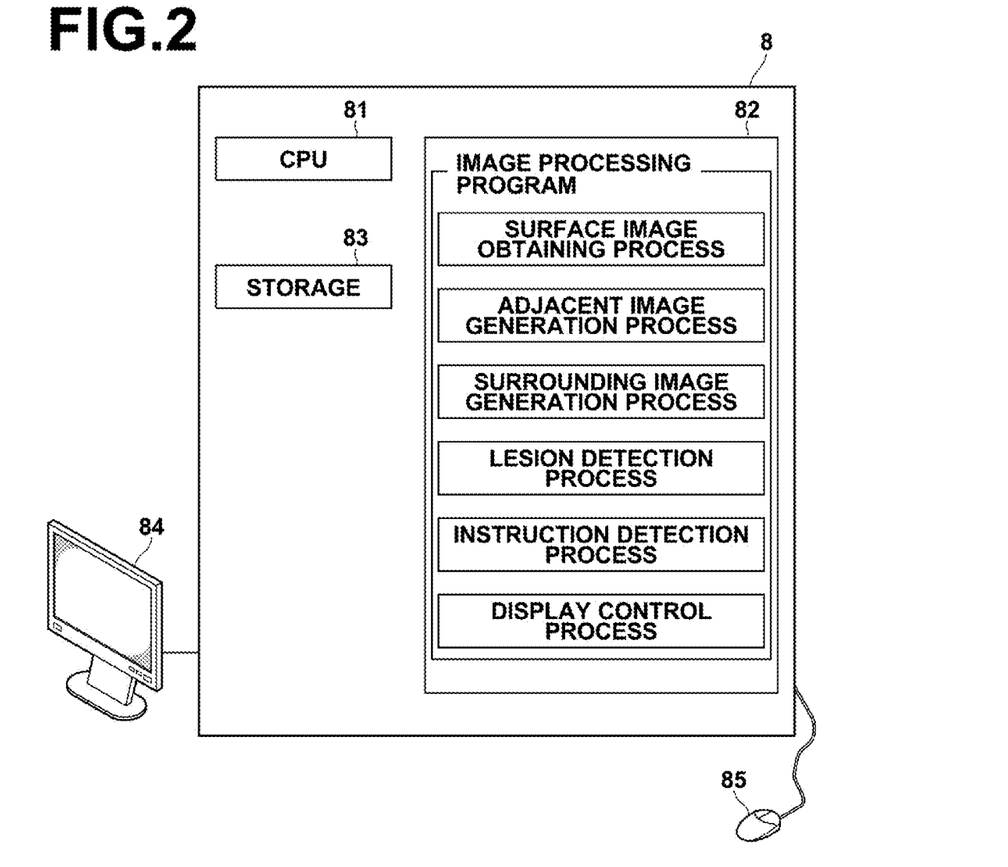
FIG. 2 schematically illustrates a configuration of the image processing apparatus shown in FIG. 1.

FIG. 2 schematically illustrates a configuration of an image processing apparatus realized by installing the image processing program on a workstation. As illustrated in the drawing, the image processing apparatus 8 includes a CPU 81, a memory 82, and a storage (image storage means) 83 as a standard configuration of workstation. Further, a display 84 and an input device (instruction detection means), such as a mouse 85 or the like, are connected to the image processing apparatus 8.

The storage 83 includes therein image data generated through image processing in the image processing apparatus 8, as well as endoscopic images and three-dimensional images obtained from the endoscope apparatus 3, three-dimensional image capturing apparatus 5, and image storage server 6 via the network 9.

Figure 3:
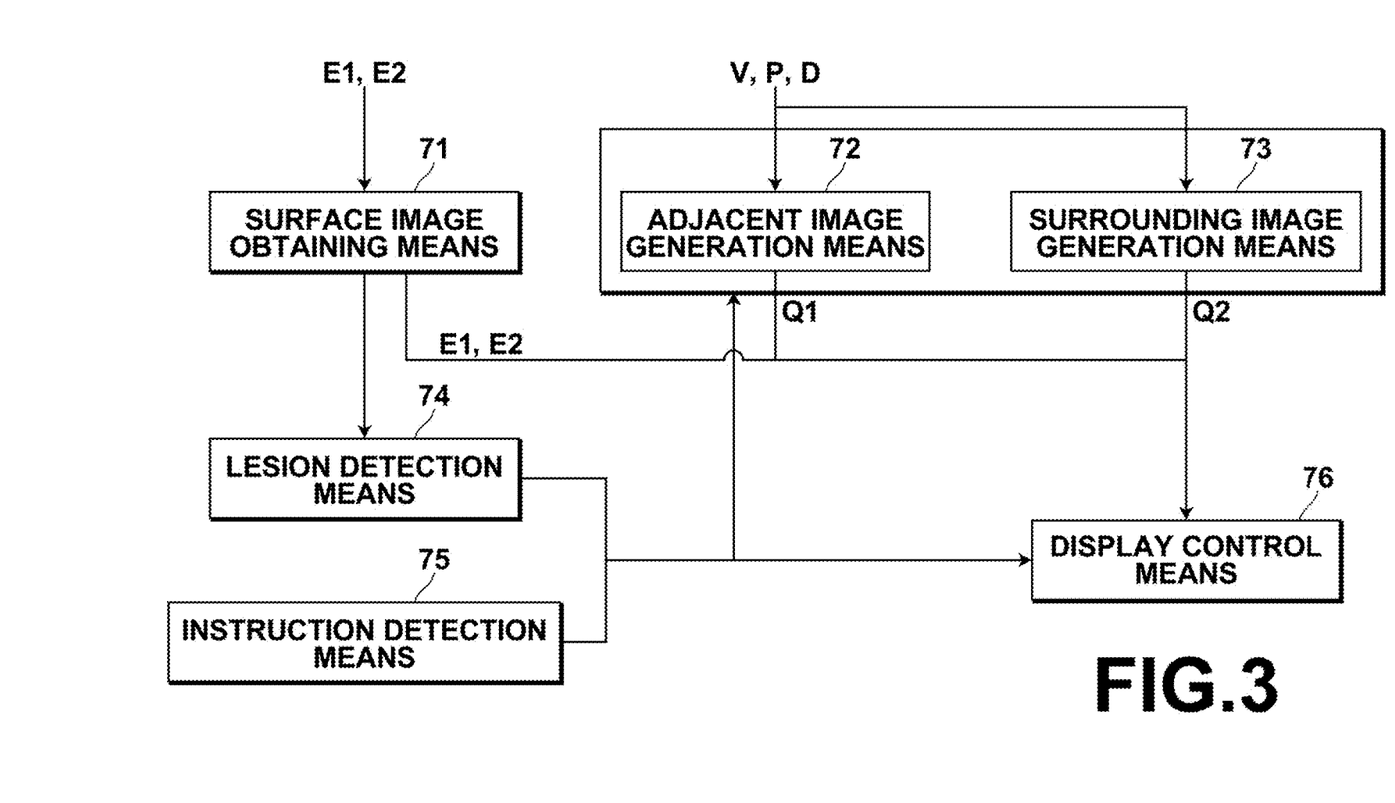
FIG. 3 is a block diagram of the image processing apparatus shown in FIG. 1, illustrating a functional configuration thereof.

The memory 82 includes therein the image processing program. The image processing program defines a surface image obtaining process, an adjacent image generation process, a surrounding image generation process, a lesion detection process, an instruction detection process, and display control process, as processes to be performed by CPU 81. Performance of these processes by the CPU 81 according to the program will cause the general purpose workstation to function as a surface image obtaining means 71, an adjacent image generation means 72, a surrounding image generation means 73, a lesion detection means 74, an instruction detection means 75, and display control means 76.

Each functional block of the image processing apparatus 8 will now be described with reference to FIG. 3.

The surface image obtaining means 71 obtains an ordinary endoscopic image E1 and a spectral endoscopic image E2 captured by imaging the inside of a large intestine at a predetermined viewpoint position by the endoscope apparatus 3. In the case where these images have already been stored in the storage 83, they may be obtained from the storage 83. Each of the ordinary endoscopic image E1 and spectral endoscopic image E2 corresponds to a surface image representing an inner surface of a wall of the large intestine. The obtained ordinary endoscopic image E1 and spectral endoscopic image E2 are outputted to the display control means 76.

The adjacent image generation means 72 generates an adjacent blood vessel image depicting a portion of a blood vessel adjacent to the large intestine wall from a viewpoint in a three-dimensional image V corresponding to the viewpoint of the ordinary endoscopic image E1 or spectral endoscopic image E2. More specifically, a three-dimensional image V is obtained from the three-dimensional image capturing apparatus 5 or image storage server 6, as well as information of position P and orientation D of the tip portion 3B (viewpoint and visual line direction of the endoscope image) attached to the ordinary endoscopic image E1 or spectral endoscopic image E2. Then, a center line of the large intestine is extracted and a plurality of lines extending radially from a point through which the center line passes on each cross-section perpendicular to the center line is set, and a pixel value of a point on an inner surface of the large intestine wall through which each line passes is set to a maximum value of those of all points on the line within a predetermined range from the surface of the wall to outside (Depth Mip mapping). This processing generates, on the inner surface of the large intestine wall, a projection image of portions of entire blood vessels having a high pixel value due to a contrast agent adjacent to the large intestine wall. Further, as the opacity allocated in the ordinary volume rendering, a value close to one is allocated to the large intestine wall so that the shape of the large intestine wall is depicted faithfully. Next, a projection image is generated from the three-dimensional image V by projecting image information on a plurality of visual lines radially extended from a viewpoint which is a position in the three-dimensional image V corresponding to the position P onto a projection plane with a direction corresponding to the orientation D as the center of the projection direction.

As for the specific projection method, a well-known volume rendering technique or the like is used (the same applies to the surrounding image generation means 73). The projection image generated in the manner as described above is a virtual endoscopic image having the same composition as that of the ordinary endoscopic image E1 or the spectral endoscopic image E2, and being an image in which a projection image of portions of blood vessels adjacent to the large intestine wall are represented on the large intestine wall as a pattern. This virtual endoscopic image corresponds to the adjacent blood vessel image of the present invention and, hereinafter, referred to as the adjacent blood vessel image. The adjacent blood vessel image is outputted to the display control means 76.

The surrounding image generation means 73 generates, from the three-dimensional image V, a surrounding blood vessel image which is an image depicting blood vessels surrounding the large intestine from a viewpoint in the three-dimensional image V corresponding to the viewpoint of the ordinary endoscopic image E1 or spectral endoscopic image E2. More specifically, a three-dimensional image V is obtained from the three-dimensional image capturing apparatus 5 or image storage server 6, as well as information of position P and orientation D of the tip portion 3B attached to the ordinary endoscopic image E1 or spectral endoscopic image E2. Further, as the opacity allocated in the ordinary volume rendering, a value close to zero is allocated to the large intestine wall so that the visibility is not obstructed by the large intestine wall. Next, a projection image is generated from the three-dimensional image V by projecting image information on a plurality of visual lines radially extended from a viewpoint which is a position in the three-dimensional image V corresponding to the position P onto a projection plane with a direction corresponding to the orientation D as the center of the projection direction. The projection image generated in the manner as described above is a pseudo three-dimensional image in which appearances of tissues surrounding the large intestine, in particular, blood vessels having a high pixel value due to a contrast agent are depicted faithfully. This pseudo three-dimensional image corresponds to the surrounding blood vessel image of the present invention and, hereinafter, referred to as the surrounding blood vessel image. The surrounding blood vessel image is outputted to the display control means 76.

The lesion detection means 74 is a means that detects a lesion from the ordinary endoscopic image E1 or spectral endoscopic image E2 and obtains a lesion area 53 by automatically detecting a lesion area, such as a projection (polyp), cancer, or tumor, with a known computer-aided diagnosis system. The lesion area may be obtained by receiving the position of a lesion detected by a doctor through interpretation of the endoscopic image and inputted using the input device, such as the mouse 85 or the like, provided in the image processing apparatus 8. A detection result of lesion is outputted to the display control means 76, adjacent image generation means 72, surrounding image generation means 73, and the like.

The instruction detection means 75 detects an input that instructs execution of a series of image display operations of the present invention, to be described later, by detecting menu selection performed by the user through the input device, such as the mouse 85 or the like. The instruction detection means 75 may be a means that detects an operation performed by the user through the operation section 3A of the endoscope apparatus 3 and detects the instruction input.

Figure 4:
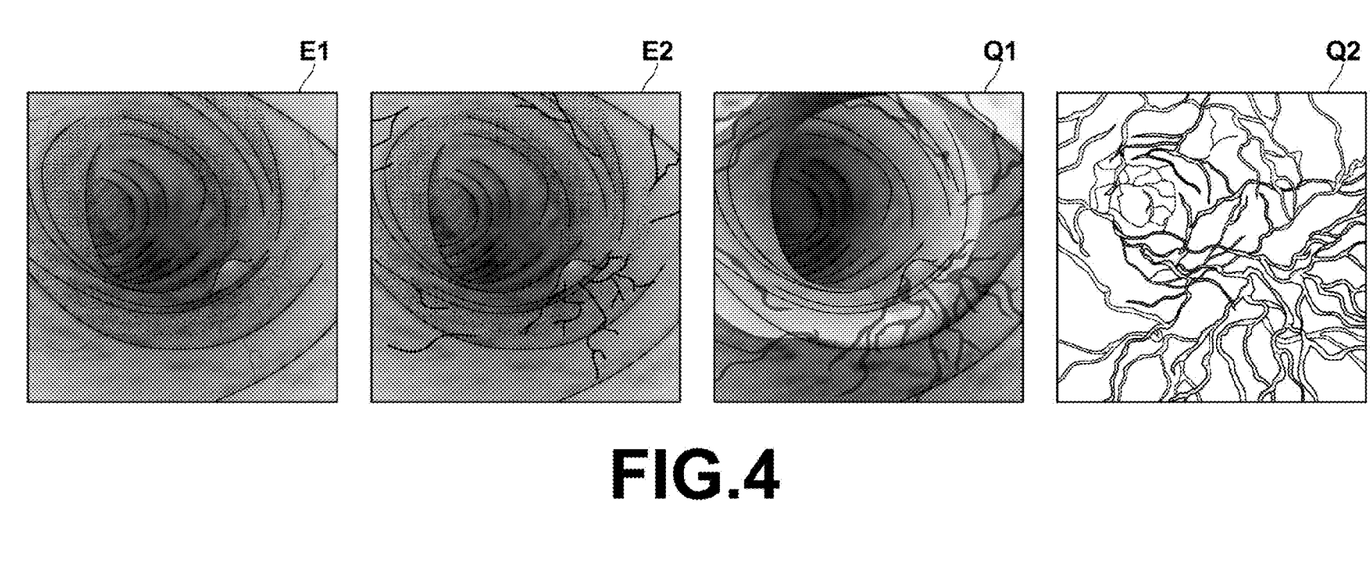
FIG. 4 illustrates a screen display, by way of example, implemented by a display control means.

The display control means 76 controls the display format and display timing of the screen of the display 84. More specifically, if the display mode is "ordinary display mode", the display control means 76 sequentially obtains and displays endoscopic images obtained by the endoscopic apparatus 3 captured at a predetermined frame rate. If the display mode is "serial display mode", the display control means 76 displays a surface image, an adjacent blood vessel image, and a surrounding blood vessel image in a switched manner in this order on a predetermined display area of the screen of the display 84. Further, the display control means 76 may also display the surface image, adjacent blood vessel image, and surrounding blood vessel image side by side from top to bottom or from left to right of the display screen. The display control means 76 determines whether to display these images in a switched manner or to display them side by side according to setting information or a user operation. FIG. 4 illustrates a display example when the display mode is "serial display mode" in which display images of ordinary endoscopic image E1, spectral endoscopic image E2, adjacent blood vessel image, and surrounding blood vessel image are displayed side by side in this order.

Further, if a lesion is detected by the lesion detection means 74 or if an input instructing to perform a serial display is detected by the instruction detection means 75, the display control means 76 sets the display mode to the "serial display mode" and performs the display described above.

Figure 5:
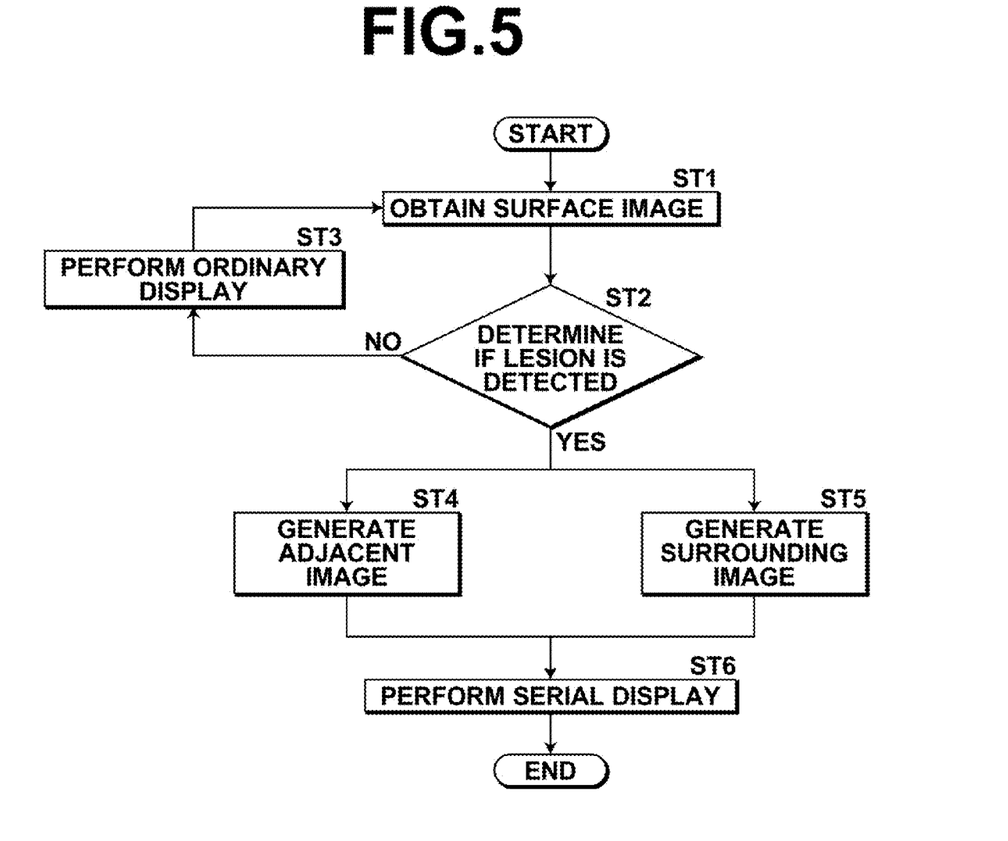
FIG. 5 is a flowchart illustrating a flow of processing performed by the image processing apparatus shown in FIG. 1.

An example of flow of processing performed by the image processing apparatus 8 of the present invention will now be described with reference to the flowchart shown in FIG. 5. First, the surface image obtaining means 71 obtains an ordinary endoscopic image E1 and a spectral endoscopic image E2 captured by imaging the inside of a large intestine at a predetermined viewpoint position by the endoscope apparatus 3 (step ST1). Thereafter, the lesion detection means 74 performs processing for detecting a lesion from the spectral endoscopic image E2 and determines wither or not a lesion is detected (step ST2). If no lesion is detected in step ST2, the display control means 76 sets the display mode to the "ordinary display mode", and sequentially obtains and displays endoscopic images obtained by the endoscopic apparatus 3 captured at a predetermined frame rate (step ST3). Thereafter, steps ST2 and ST3 are repeated until a lesion is detected in step ST2.

If a lesion is detected in step ST2, the adjacent image generation means 72 generates, from the three-dimensional image V, an adjacent blood vessel image which is an image depicting portions of blood vessels adjacent to the large intestine wall from a viewpoint in the three-dimensional image V corresponding to the viewpoint of the ordinary endoscopic image E1 (step ST4). In addition, the surrounding image generation means 73 generates, from the three-dimensional image V, a surrounding blood vessel image which is an image depicting blood vessels surrounding the large intestine from a viewpoint in the three-dimensional image V corresponding to the viewpoint of the ordinary endoscopic image E1 (step ST5). Steps ST5 and ST6 may be performed at the same time, or either one may be performed first and the other may be performed next. Subsequently, the display control means 76 sets the display mode to the "serial display mode" and displays the ordinary endoscopic image E1, spectral endoscopic image E2, adjacent blood vessel image, and surrounding blood vessel image in a switched manner in this order (step ST6), and the processing is completed.

As described above, according to the image processing apparatus and program of the present embodiment, endoscopic images (surface images) E1, E2 representing an inner surface of a large intestine wall are obtained by image capturing performed by an endoscope inserted into the large intestine. Then, from a three-dimensional image representing a three-dimensional area including the large intestine, an adjacent blood vessel image Q1 which is an image depicting portions of blood vessels adjacent to the large intestine wall from a viewpoint in the three-dimensional image corresponding to the viewpoint of the endoscopic image and a surrounding blood vessel image Q2 which is an image depicting surrounding blood vessels from the viewpoint in the three-dimensional image corresponding to the viewpoint of the endoscopic image are generated. Thereafter, the endoscopic images E1, E2, adjacent blood vessel image Q1, and surrounding blood vessel image Q2 are displayed in this order on a display means. This allows the appearance of the inner surface of the large intestine and the appearance of a blood vessel running from the surface to an outer periphery to be observed continuously whereby the relationship between a tissue on the inner surface of the large intestine and a surrounding blood vessel associated with the large intestine may be understood easily.

Further, lesion detection is performed on the endoscopic image and if a lesion, such as a polyp, is detected, the endoscopic images, adjacent blood vessel image, and surrounding blood vessel image are caused to be displayed in this order on the display means. This allows the appearance of a blood vessel supplying nourishment to the lesion and the running of the succeeding major blood vessel, as well as the appearance of the lesion on the mucosal surface, to be observed easily, thereby facilitating a determination as to whether the lesion is benign or malignant and surgical planning.

In the embodiment described above, the description has been made of a case in which the image processing apparatus of the present invention is applied to observe a large intestine, but the application is not limited to this and the apparatus may also be used to observe other tubular organs, such as a stomach, associated with surrounding blood vessels.

Further, in the embodiment described above, the description has been made of a case in which both the ordinary endoscopic image E1 and spectral endoscopic image E2 are displayed as surface images, but an arrangement may be adopted in which only either one of them is displayed.

Still further, the display control means 76 may be a means further equipped with a function to display the surrounding blood vessel image Q2, adjacent blood vessel image Q1, and surface images E1, E2 on a predetermined display area of the screen of the display 84 in a switched manner in this order which is reverse to the serial image display order described above by further detecting a menu selection performed by the user through the input device, such as the mouse 85 or the like, when the display mode is "serial display mode".

Further, the image processing apparatus 8 described above may further include an image generation means that generates, from the three-dimensional image V, a virtual endoscopic image having the same composition as that of the endoscopic image captured by the endoscope apparatus 3 and representing the appearance of a target organ in a manner as if it were observed by an endoscope, and when the display mode is "normal display mode", the endoscopic image and virtual endoscopic image having the same composition as that of the endoscopic image generated by the image generation means may be displayed in an interlocking manner by the display control means 76.

What is claimed is:

1. An image processing apparatus for displaying an image for observing a tubular organ associated with a surrounding blood vessel, the apparatus comprising:
a surface image obtaining unit configured to obtain a first image which is a surface image representing an inner surface of a wall of the tubular organ captured by an endoscope inserted in the organ, the surface image being either one or both of a normal endoscopic image captured when white light is directed to the inner surface of the wall of the tubular organ or a spectral endoscopic image captured when light in a specific wavelength range different from the white light is directed to the inner surface of the wall of the tubular organ;
an adjacent image generation unit configured to automatically generate a second image which is an adjacent blood vessel image from a first three-dimensional image representing a first three-dimensional area including the tubular organ, the adjacent blood vessel image being an image depicting a portion of the blood vessel within a predetermined range from the inner surface of the wall of the tubular organ to outside from a viewpoint in the first three-dimensional image corresponding to a viewpoint of the surface image;
a surrounding image generation unit configured to automatically generate a third image which is a surrounding blood vessel image from a second three-dimensional image representing a second three-dimensional area including a surrounding area of the tubular organ, the third image being an image depicting the blood vessel without displaying the wall of the organ, the surrounding blood vessel image being an image depicting the blood vessel within a range wider than the predetermined range;
a display control unit configured to automatically cause the first image, the second image, and the third image to be displayed in this order on a display unit, so as to allow an appearance of the inner surface of the wall of the tubular organ and an appearance of a blood vessel running from the inner surface of the wall of the tubular organ to an outer surface of the wall to be observed continuously;
a three dimensional image capturing apparatus which is a CT (computer tomography) apparatus, MRI (magnetic resonance imaging) apparatus, PET (positron emission tomography), or ultrasonograph;
the adjacent blood vessel image is an image that depicts blood vessels of tissue positioned from the inner surface of the wall of the tubular organ where the wall of the tubular organ has an opacity so that the shape of the large intestine wall is depicted; and
the surrounding blood vessel image is an image that depicts blood vessels of tissue positioned from the inner surface of the wall of the tubular organ,
wherein the adjacent blood vessel image and the surrounding blood vessel image are obtained by maximum intensity projection (MIP) depth mapping from the three-dimensional image, information of position and orientation of a tip portion of the endoscope, to give a viewpoint and visual line direction of the endoscopic image, attached to the ordinary endoscopic image or spectral endoscopic image, and a center line of the tubular organ is extracted and a plurality of lines extending radially from a point through which a center line passes on each cross-section perpendicular to the center line is set, and a pixel value of a point on an inner surface of the tubular organ wall through which each line passes is set to a maximum value, in the case of the adjacent blood vessel image, of those of all points on the line within a predetermined range from the inner surface of the wall to the outer surface of the wall, and in the case of the surrounding blood vessel image, to a value where the visibility is not obstructed by the wall of the tubular organ.

2. The image processing apparatus of claim 1, wherein:
the apparatus comprises a lesion detection unit configured to detect a lesion from the surface image; and
the display control unit is a unit configured to cause an image to be displayed when a lesion is detected.

3. The image processing apparatus of claim 1, wherein:
the apparatus comprises an instruction detection unit configured to detect an input that instructs execution of the image display; and
the display control unit is a unit configured to cause an image display to be performed when the input is detected by the instruction detection unit.

4. The image processing apparatus of claim 1, wherein the display control unit is a unit configured to cause the surface image, adjacent blood vessel image, and surrounding blood vessel image to be displayed in a switched manner.

5. The image processing apparatus of claim 1, wherein the display control unit is a unit configured to cause the first image, the second image, and the third image to be displayed side by side.

6. The image processing apparatus of claim 1, wherein the second image is an image representing the portion of the blood vessel projected onto a structure of the organ.

7. An image display method for displaying an image for observing a tubular organ associated with a surrounding blood vessel, the method comprising:
a surface image obtaining process for obtaining first image which is a surface image representing an inner surface of a wall of the tubular organ captured by an endoscope inserted in the organ, the surface image being either one or both of a normal endoscopic image captured when white light is directed to the inner surface of the wall of the tubular organ or a spectral endoscopic image captured when light in a specific wavelength range different from the white light is directed to the inner surface of the wall of the tubular organ;
an adjacent image generation process for automatically generating a second image which is an adjacent blood vessel image from a three-dimensional image representing a first three-dimensional area including the tubular organ, the adjacent blood vessel image being an image depicting a portion of the blood vessel within a predetermined range from the inner surface of the wall of the tubular organ to outside from a viewpoint in the first three-dimensional image, which corresponds to a viewpoint of the surface image;
a surrounding image generation process for automatically generating a third image which is a surrounding blood vessel image from a second three-dimensional image representing a three-dimensional area including a surrounding area of the tubular organ, the third image being an image depicting the blood vessel without displaying the wall of the organ, the surrounding blood vessel image being an image depicting the blood vessel within a range wider than a predetermined range;
a display control process for automatically causing the first image, the second image, and the third image to be displayed in this order on a display unit, so as to allow an appearance of the inner surface of the wall of the tubular organ and an appearance of a blood vessel running from the inner surface of the wall of the tubular organ to an outer surface of the wall to be observed continuously;
a three dimensional image capturing apparatus which is a CT (computer tomography) apparatus, MRI (magnetic resonance imaging) apparatus, PET (positron emission tomography), or ultrasonograph,
the adjacent blood vessel image is an image that depicts blood vessels of tissue positioned from the inner surface of the wall of the tubular organ where the wall of the tubular organ has an opacity so that the shape of the large intestine wall is depicted; and
the surrounding blood vessel image is an image that depicts blood vessels of tissue positioned from the inner surface of the wall of the tubular organ,
wherein the adjacent blood vessel image and the surrounding blood vessel image are obtained by maximum intensity projection (MIP) depth mapping from the three-dimensional image, information of position and orientation of a tip portion of the endoscope, to give a viewpoint and visual line direction of the endoscopic image, attached to the ordinary endoscopic image or spectral endoscopic image, and a center line of the tubular organ is extracted and a plurality of lines extending radially from a point through which a center line passes on each cross-section perpendicular to the center line is set, and a pixel value of a point on an inner surface of the tubular organ wall through which each line passes is set to a maximum value, in the case of the adjacent blood vessel image, of those of all points on the line within a predetermined range from the inner surface of the wall to the outer surface of the wall, and in the case of the surrounding blood vessel image, to a value where the visibility is not obstructed by the wall of the tubular organ.

8. The image display method of claim 7, wherein:
the method comprises a lesion detection process for detecting a lesion from the surface image; and
the display control process is a process that causes an image to be displayed when a lesion is detected.

9. A non-transitory computer readable medium on which is recorded an image processing program for displaying an image for observing a tubular organ associated with a surrounding blood vessel, the program causing a computer to function as:
a surface image obtaining unit configured to obtain a first image which is a surface image representing an inner surface of a wall of the tubular organ captured by an endoscope inserted in the organ, the surface image being either one or both of a normal endoscopic image captured when white light is directed to the inner surface of the wall of the tubular organ or a spectral endoscopic image captured when light in a specific wavelength range different from the white light is directed to the inner surface of the wall of the tubular organ;
an adjacent image generation unit configured to automatically generate a second image which is an adjacent blood vessel image from a first three-dimensional image representing a first three-dimensional area including the tubular organ, the adjacent blood vessel image being an image depicting a portion of the blood vessel within a predetermined range from the inner surface of the wall of the tubular organ to outside from a viewpoint in the first three-dimensional image, which corresponds to a viewpoint of the surface image;

a surrounding image generation unit configured to automatically generate a third image which is a surrounding blood vessel image from a second three-dimensional image representing a second three-dimensional area including a surrounding area of the tubular organ, the third image being an image depicting the blood vessel without displaying the wall of the organ, the surrounding blood vessel image being an image depicting the blood vessel within a range wider than the predetermined range;

a display control unit configured to automatically cause the first image, the second image, and the third image to be displayed in this order on a display unit, so as to allow an appearance of the inner surface of the wall of the tubular organ and an appearance of a blood vessel running from the inner surface of the wall of the tubular organ to an outer surface of the wall to be observed continuously;

a three dimensional image capturing apparatus which is a CT (computer tomography) apparatus, MRI (magnetic resonance imaging) apparatus, PET (positron emission tomography), or ultrasonograph;

the adjacent blood vessel image is an image that depicts blood vessels of tissue positioned from the inner surface of the wall of the tubular organ where the wall of the tubular organ has an opacity so that the shape of the large intestine wall is depicted; and the surrounding blood vessel image is an image that depicts blood vessels of tissue positioned from the inner surface of the wall of the tubular organ, wherein the adjacent blood vessel image and the surrounding blood vessel image are obtained by maximum intensity projection (MIP) depth mapping from the three-dimensional image, information of position and orientation of a tip portion of the endoscope, to give a viewpoint and visual line direction of the endoscopic image, attached to the ordinary endoscopic image or spectral endoscopic image, and a center line of the tubular organ is extracted and a plurality of lines extending radially from a point through which a center line passes on each cross-section perpendicular to the center line is set, and a pixel value of a point on an inner surface of the tubular organ wall through which each line passes is set to a maximum value, in the case of the adjacent blood vessel image, of those of all points on the line within a predetermined range from the inner surface of the wall to the outer surface of the wall, and in the case of the surrounding blood vessel image, to a value where the visibility is not obstructed by the wall of the tubular organ.

10. The non-transitory computer readable medium of claim 9, wherein:
the program further causes the computer to function as a lesion detection unit configured to detect a lesion from the surface image; and
the display control unit is a unit configured to cause an image to be displayed when a lesion is detected.

11. The image processing apparatus of claim 1, wherein:
the third image is an image depicting the blood vessel without displaying the wall of the organ.

12. The image display method of claim 7, wherein:
the third image is an image depicting the blood vessel without displaying the wall of the organ.

13. The non-transitory computer readable medium of claim 9, wherein:
the third image is an image depicting the blood vessel without displaying the wall of the organ.

14. The image processing apparatus of claim 1, wherein:
a projection image of the adjacent image is generated from the three-dimensional image by projecting image information on the plurality of visual lines radially extended from the viewpoint which is a position in the three dimensional image corresponding to the position onto a projection plane with a direction corresponding to the orientation as a center of the projection direction.

15. The image display method of claim 7, wherein:
a projection image of the adjacent image is generated from the three-dimensional image by projecting image information on the plurality of visual lines radially extended from the viewpoint which is a position in the three dimensional image corresponding to the position onto a projection plane with a direction corresponding to the orientation as a center of the projection direction.

16. The non-transitory computer readable medium of claim 9, wherein:
a projection image of the adjacent image is generated from the three-dimensional image by projecting image information on the plurality of visual lines radially extended from the viewpoint which is a position in the three dimensional image corresponding to the position onto a projection plane with a direction corresponding to the orientation as a center of the projection direction.

* * * * *